United States Patent

Konz et al.

Patent Number: 5,817,814
Date of Patent: Oct. 6, 1998

[54] METHOD FOR THE PREPARATION OF BENZYLURACILS

[75] Inventors: Marvin J. Konz, Yardley, Pa.; Harvey R. Wendt, Southampton, N.J.

[73] Assignee: FMC Corporation, Philadelphia, Pa.

[21] Appl. No.: 846,472

[22] Filed: May 1, 1997

[51] Int. Cl.⁶ .................................................. C07D 239/54
[52] U.S. Cl. ........................... 544/309; 544/312; 544/314
[58] Field of Search ..................................... 544/309, 312, 544/314

[56] References Cited

U.S. PATENT DOCUMENTS

| | | | |
|---|---|---|---|
| 3,580,913 | 5/1971 | Lutz | 260/260 |
| 5,391,541 | 2/1995 | Konz | 504/243 |

FOREIGN PATENT DOCUMENTS 92300543  7/1992  European Pat. Off. .

*Primary Examiner*—John M. Ford
*Attorney, Agent, or Firm*—J. Robert Silverman; Joseph Lucci; Donald J. Silvert

[57] ABSTRACT

This invention describes a method for preparing benzyluracils using methyl benzylcarbamates as intermediates. The method comprises the steps of contacting an alkali metal salt of an ester of 3-amino-4,4,4-trifluoro-2-butenoic acid with a methyl benzylcarbamate I to provide a benzyluracil II.

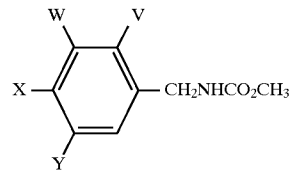

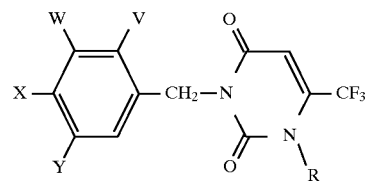

where R, W, V, X and Y are as described in the specification.

6 Claims, No Drawings

METHOD FOR THE PREPARATION OF BENZYLURACILS

BACKGROUND OF THE INVENTION

This invention relates generally to a method for preparing benzyluracils. In particular, it relates to a method for preparing benzyluracils using methyl benzylcarbamates as intermediates. More particularly, it relates to a method for preparing 3-(substituted-benzyl)-6-trifluoromethyl-2,4(1H,3H)-pyrimidinediones. Most particularly, it relates to a method for preparing 1-methyl-3-(substituted-benzyl)-6-trifluoromethyl-2,4(1H,3H)-pyrimidinediones.

It is known that certain compounds having a uracil or pyrimidinedione moiety have significant herbicidal activity (see for example, European Patent Application publication number 0 496 595 A1, U.S. Pat. No. 5,169,431, and U.S. Pat. No. 5,521,147). The chemical structure of most of these herbicides is such that the uracil moiety is attached directly to a phenyl or other aromatic ring.

Synthesis of the uracil moiety is typically achieved by treating either an aryl isocyanate or aryl carbamate with an amino crotonate ester and a base. For example, a synthesis using ethyl 3-amino-4,4,4-trifluoro-2-butenoate as the crotonate ester is described in U.S. Pat. No. 5,169,431 and shown below:

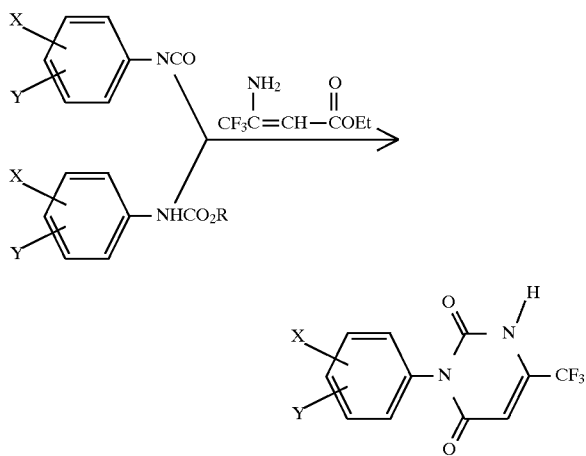

Recently, herbicidal uracils have been reported where the uracil moiety is separated from a phenyl ring by a methylene group to provide benzyluracils. For example, herbicidal benzyluracils described in U.S. Pat. No. 5,391,541 (FMC Corporation) have the generic structure:

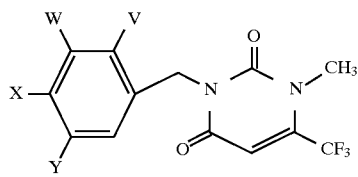

in which V is hydrogen or halogen; W is hydrogen, halogen, lower alkoxy, lower alkylaminocarbonyl, propargyloxy, or cyano; X is hydrogen or chlorine; and Y is hydrogen, halogen, cyano, lower alkylaminocarbonyl, or carboxy. These compounds were generally prepared by treating the appropriately substituted benzyl isocyanate with ethyl 3-amino4,4,4-trifluoro-2-butenoate as described above. U.S. Pat. No. 5,391,541 also discloses that these compounds may be prepared starting with the corresponding ethyl carbamate in place of the isocyanate.

It has now been found that surprisingly higher yields of benzyluracils are obtained when a "methyl" benzylcarbamate as opposed to an "ethyl" benzylcarbamate is treated with a crotonate ester.

SUMMARY OF THE INVENTION

This invention describes a method for preparing benzyluracils using methyl benzylcarbamates as intermediates. The method comprises the steps of contacting an alkali metal salt of an ester of 3-amino-4,4,4-trifluoro-2-butenoic acid with a methyl benzylcarbamate I to provide a benzyluracil II.

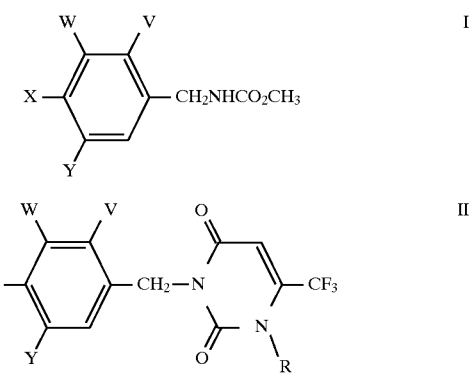

where R, W, V, X and Y are as described in the specification.

DETAILED DESCRIPTION OF THE INVENTION

This invention describes a method for preparing benzyluracils using methyl benzylcarbamates as intermediates. Surprisingly, it has been found that a "methyl" benzylcarbamate in particular, when treated with an ester of 3-amino-4,4,4-trifluoro-2-butenoic acid, provides high yields of benzyluracils of formula II below.

The method comprises the steps of taking an ester of 3-amino-4,4,4-trifluoro-2-butenoic acid, forming an alkali metal salt of the ester, contacting the salt in the presence of a suitable solvent with a methyl (optionally substituted-benzyl)carbamate of formula I to provide a benzyluracil of formula II:

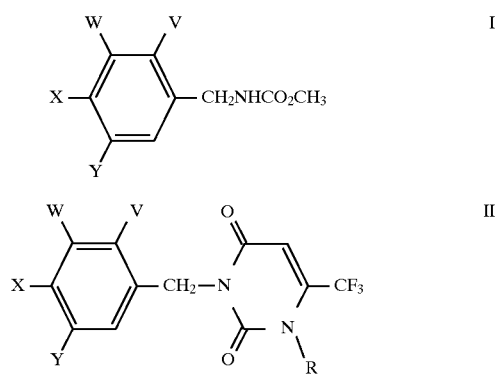

in which V is hydrogen, halogen, nitro, amino, alkoxy, alkyl, cyano, phenyl, alkylcarbonylamino, alkylsulfinyl, or haloalkyl;

W is hydrogen, halogen, alkyl, alkoxy, alkylaminocarbonyl, propargyloxy, cyano, nitro, benzoyl, aminooxycarbonyl, alkylsulfonyl, alkoxyiminoalkyl, alkylthio, or alkylsulfinyl;

X is hydrogen, chlorine, alkoxy, nitro, or amino;

Y is hydrogen, halogen, alkyl, haloalkyl, alkoxy, haloalkoxy, alkoxyalkyl, alkylthio, alkylthioalkyl, alkenyl, acyl, epoxyalkyl, cyano, alkylaminocarbonyl, carboxy, formyl, hydroxy, hydroxyalkyl, haloalkylsulfonyloxy, benzoyl, aminooxycarbonyl, alkoxycarbonyl, propargyloxy, alkylsulfonyl, alkylsulfinyl, alkoxyiminoalkyl, dialkylaminocarbonylthio, or X and Y taken together are —OCH$_2$O— or —OC(CH$_3$)$_2$O—; and R is hydrogen, sodium, potassium, lithium, barium or calcium.

Another aspect of the invention comprises the same steps as above and the further step of contacting II with a methylating agent in the presence of a suitable solvent to provide II where R is methyl.

A particular aspect of the invention relates to a method comprising the steps of taking an alkyl 3-amino4,4,4-trifluoro-2-butenoate ester, forming an alkali metal salt of the butenoate ester, contacting the salt in the presence of a suitable solvent with a methyl (optionally substituted-phenylmethyl)carbamate of formula I to provide a benzyluracil of formula II in which V is chlorine, W is chlorine or methoxy, X is hydrogen, and Y is chlorine or methoxy. A more particular aspect of the invention relates to a method in which V and Y are chlorine and W is methoxy.

The methyl benzylcarbamates which are useful as starting materials for the method of this invention are novel compositions and include compounds of formula I:

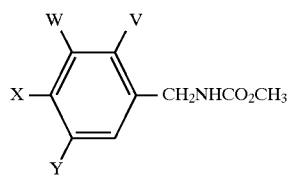

in which V is hydrogen, halogen, nitro, amino, alkoxy, alkyl, cyano, phenyl, alkylcarbonylamino, alkylsulfinyl, or haloalkyl;

W is hydrogen, halogen, alkyl, alkoxy, alkylaminocarbonyl, propargyloxy, cyano, nitro, benzoyl, aminooxycarbonyl, alkylsulfonyl, alkoxyiminoalkyl, alkylthio, or alkylsulfinyl;

X is hydrogen, chlorine, alkoxy, nitro, or amino;

Y is hydrogen, halogen, alkyl, haloalkyl, alkoxy, haloalkoxy, alkoxyalkyl, alkylthio, alkylthioalkyl, alkenyl, acyl, epoxyalkyl, cyano, alkylaminocarbonyl, carboxy, formyl, hydroxy, hydroxyalkyl, haloalkylsulfonyloxy, benzoyl, aminooxycarbonyl, alkoxycarbonyl, propargyloxy, alkylsulfonyl, alkylsulfinyl, alkoxyiminoalkyl, dialkylaminocarbonylthio, or X and Y taken together are —OCH$_2$O— or —OC(CH$_3$)$_2$O.

One aspect of the present invention relates to compounds of formula I in which V is chlorine, W is chlorine or methoxy, X is hydrogen, and Y is chlorine or methoxy. A more particular aspect of the invention relates to a compound of formula I in which V and Y are chlorine and W is methoxy.

As used in this specification and unless otherwise indicated, the terms "alkyl," "alkenyl," "alkynyl," "haloalkyl," and "alkoxy" used alone or as part of a larger moiety, includes straight or branched carbon chains of 1 to 6 carbon atoms. "Halogen" refers to fluorine, bromine or chlorine. "THF" means tetrahydrofuran, "DMF" means N,N-dimethylformamide, and "DMSO" means dimethylsulfoxide. "Alkali metal" means sodium, potassium, lithium, barium or calcium.

The preparation of methyl benzylcarbamates of formula I may be accomplished by methods similar to those known in the art for preparing alkylcarbamates. U.S. Pat. No. 5,391,541 teaches the preparation of the starting benzylamines. In a typical procedure for obtaining the methyl benzylcarbamates, an appropriate benzylamine is stirred in a suitable solvent with a slight molar excess of an organic amine base. The reaction mixture is then cooled between about −10° C. and 10° C., and about one molar equivalent of a methyl chloroformate is added at a rate to maintain the reaction mixture at a temperature in that range. After about one-half hour to two hours, the reaction mixture is allowed to warm to ambient temperature where it stirs for an additional two to 24 hours. Isolation of reaction product generally provides the methyl benzylcarbamate in excellent yields, typically around 80 to 95%.

Suitable solvents for converting the benzylamines to benzylcarbamates include, but are not limited to, toluene, DMF, DMSO, methylene chloride, ether and THF, with THF being preferred. Organic amine bases that may be used include pyridine, triethylamine, N,N-dialkylanilines, and 4-(N,N-dimethylamino)pyridine, with triethylamine being preferred. The amount of base that is required is usually in the molar range of 1.0 to 1.5 equivalents per equivalent of benzylamine.

The ester of 3-amino-4,4,4-trifluoro-2-butenoic acid used to form the uracil moiety has the following structure:

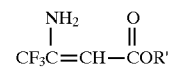

where R' is alkyl or phenyl.

A preferred butenoate ester is ethyl 3-amino4,4,4-trifluoro-2-butenoate. To form the alkali metal salt of the butenoate or crotonate ester III, III is treated with a base such as an alkali metal hydride, alkali metal hydroxide, or an alkali metal carbonate in a suitable solvent. Examples of such bases include sodium hydride, potassium hydride, sodium carbonate, potassium carbonate, barium carbonate, calcium carbonate, calcium hydroxide and barium hydroxide. Suitable solvents include aromatic hydrocarbons such as toluene, polar solvents such as DMF and DMSO, halogenated solvents such as methylene chloride, and ethers such as diethyl ether and THF. Preferred solvents are those with a boiling point in the temperature range of 60° C. to 200° C. A particularly preferred solvent is DMF. A preferred alkali metal salt is the potassium or sodium salt of the crotonate ester III. Particularly preferred is the potassium or sodium salt of an alkyl 3-amino-4,4,4-trifluoro-2-butenoate. More particularly preferred is the potassium or sodium salt of ethyl 3-amino-4,4,4-trifluoro-2-butenoate.

The cyclization reaction to form the uracil moiety is conducted in about 0.5 to six hours. In a preferred method, the reaction is carried out by adding the methyl benzylcarbamate to the alkali metal salt of the alkyl 3-amino-4,4,4-trifluoro-2-butenoate. A preferred amount of crotonate salt is about 1.0 to 1.2 molar equivalents per equivalent of benzylcarbamate. During the addition of the methyl benzylcarbamate the reaction temperature is maintained in the range of about −10° C. to 10° C., most preferably at about 5° C. Upon completion of the addition, the reaction mixture stirs for a period of time, preferably for about one hour at about 5° C. The reaction mixture is warmed to about 80° C. to 150°

C., preferably to about 95° C., where it stirs until the cyclization is complete, usually within about 0.5 to six hours after being warmed. The resulting 1-unsubstituted-6-trifluoromethyl-3-(substituted benzyl)-2,4(1H,3H) pyrimidinedione alkali metal salt may, without isolation, be N-alkylated in-situ, i.e., in the same reaction vessel. Alternatively, the unsubstituted benzyl uracil may be isolated from the reaction mixture after the salt is quenched following a standard aqueous work-up procedure.

In-situ N-alkylation of the 1-unsubstituted-6-trifluoromethyl-3-(appropriately substituted phenylmethyl)-2,4(1H,3H)pyrimidinedione alkali metal salt is carried out under basic conditions in about 0.5 to 30 hours. In a preferred method a methylating agent is added to the pyrimidinedione alkali metal salt at a reaction mixture temperature between about −5° C. to 10° C., most preferably at about 5° C. Examples of suitable methylating agents are dimethylsulfate and methyl halides such as methyl iodide. A preferred methylating agent is methyl iodide. The amount of methylating agent required to complete the reaction is about 1.5 to 2.5 molar equivalents per equivalent of pyrimidinedione alkali metal salt. To ensure the basicity of the reaction mixture, the addition of 0.1 to 1.0 molar equivalents of an inorganic base, such as potassium carbonate, may be required before and during the N-alkylation process. Upon completion of addition of the methylating agent, the reaction mixture stirs at an elevated temperature between about 20° C. to 60° C., preferably at a temperature between ambient temperature to 40° C. Alkylation is usually complete within about two to 24 hours at the elevated temperature.

The Examples below provide a detailed description of certain aspects of the present invention. It is apparent that various modifications may be made in carrying out the methods of this invention without departing from the inventive concepts herein as defined in the claims.

EXAMPLE 1

SYNTHESIS OF 1-METHYL-6-TRIFLUOROMETHYL-3-(2,3-DICHLORO-5-METHOXYPHENYLMETHYL)-2,4(1H,3H)-PYRIMIDINEDIONE

Step A Synthesis of methyl (2,3-dichloro-5-methoxyphenylmethyl)carbamate

A stirred solution of 54.0 grams (0.262 mole) of 2,3-dichloro-5-methoxy-phenylmethylamine and 27.0 grams (0.267 mole) of triethylamine in 1000 mL of THF was cooled below 5° C., and 24.8 grams (0.262 mole) of methyl chloroformate was added dropwise at a rate to maintain the reaction mixture temperature below 5° C. Upon completion of addition, the reaction mixture was stirred at about 5° C. for one hour, then it was allowed to warm to ambient temperature as it stirred for about 18 hours. After this time thin layer chromatographic (TLC) analysis of the reaction mixture indicated the reaction was complete. The reaction mixture was concentrated under reduced pressure to a residue, which was then shaken with ethyl acetate and water. The aqueous layer was washed with ethyl acetate, and the wash was combined with the original organic layer. The combination was then washed with one portion of water and one portion of an aqueous saturated sodium chloride solution. The organic layer was dried with sodium sulfate, filtered, and concentrated under reduced pressure, yielding 66.0 grams (95.3% yield) of the subject compound, mp 90°–91° C. (99% pure by gas chromatographic (GC) analysis). The NMR spectrum was consistent with the proposed structure.

Step B Synthesis of 1-methyl-6-tifluoromethyl-3-(2,3-dichloro-5-methoxyphenylmethyl)-2,4(1H,3H)-pyrimidinedione Under a nitrogen atmosphere, a stirred suspension of 12.4 grams (0.310 mole) of 60% sodium hydride (in mineral oil) in 100 mL of DMF was cooled below 5° C., and a solution of 47.7 grams (0.260 mole) of ethyl 3-amino-4,4,4-trifluoro-2-butenoate in 50 mL of DMF was added dropwise at a rate to maintain the reaction mixture temperature below 10° C. Upon completion of addition, the reaction mixture was stirred for 10 minutes while being cooled to below 5° C. After this time, a slurry of 65.4 grams (0.248 mole) of methyl (2,3-dichloro-5-methoxyphenylmethyl)carbamate in 130 mL of DMF was added at a rate to maintain the reaction mixture temperature below 5° C. Upon completion of addition, the reaction mixture was stirred for one hour at about 5° C., then it was heated to 95° C. where it stirred for three hours. GC and TLC analysis of the reaction mixture indicated that the reaction was complete.

The nitrogen flow was discontinued, the stirred reaction mixture was again cooled to about 5° C., and 6.9 grams (0.050 mole) of potassium carbonate was added. The reaction mixture was stirred for five minutes, and 52.8 grams (0.372 mole) of methyl iodide was added. The resultant reaction was exothermic, which was controlled with an ice-water bath. When the exotherm subsided, the reaction mixture was allowed to warm to ambient temperature as it stirred for about 18 hours. After this time TLC analysis of the reaction mixture indicated that the reaction had not gone to completion. An additional 27.0 grams (0.195 mole) of potassium carbonate and 35.0 grams (0.241 mole) of methyl iodode were added, and the reaction mixture was stirred at 40° C. for about five hours. After this time the reaction mixture was poured into 3000 mL of ice-water, which was then stirred for 15 minutes. The mixture was filtered through a sintered glass funnel to collect a solid. The solid was triturated twice with 1500 mL portions each of water. The solid was then stirred with about 1500 mL of ethyl acetate, and the resultant solution was filtered to remove a small amount of insoluble material. The filtrate was placed in a separatory funnel and washed with two portions of an aqueous saturated sodium chloride solution. The organic layer was dried with sodium sulfate and filtered. The filtrate was concentrated under reduced pressure, yielding about 90.1 grams of solid that was 95% pure by GC analysis. The solid was combined with 7.6 grams of product from a prior, small run (0.0223 mole) of this reaction. The combined 97.7 grams of brown solid was treated with decolorizing carbon and recrystallized from hexane/ethyl acetate. The resultant off-white solid was collected by filtration and washed with hexane. The solid was then triturated with 500 mL of 2% ethyl acetate in hexane. The solid was collected by filtration and dried under vacuum, yielding 62.8 grams of the subject compound, mp 144°–144.5° C. The NMR spectrum was consistent with the proposed structure. The organic filtrates were combined and concentrated under reduced pressure to a residual solid. The solid was recrystallized from hexane/ethyl acetate. The resultant tan solid was collected by filtration, washed with hexane, and triturated with 200 mL of 4% ethyl acetate in hexane. The solid was again collected by filtration, yielding 19.4 grams of the subject compound, mp 143.5°–144.5° C. The NMR spectrum was consistent with the proposed structure. The two solids were combined for a total yield of 82.2 grams of subject compound (78.7% yield based on a combined theoretical yield of 104.5 grams from the small 0.0223 mole run and the 0.248 mole run exemplified here).

TABLE 1

Comparison of Methyl- and Ethylcarbamates

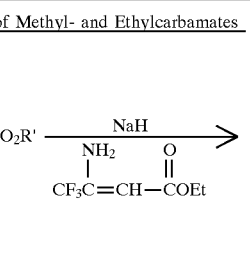

Ia, R' = CH₃
Ib, R' = CH₂CH₃

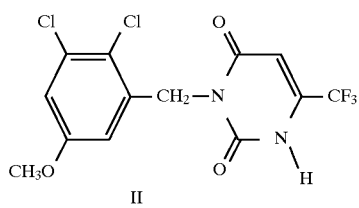

| Starting Material | % Yield of II[a] |
|---|---|
| Ia | 76[b] |
| Ib | 51[c] |

[a] Yield of purified II
[b] Yield is the average of three reactions
[c] % Yield is the average of two reactions Table 1 shows the effect of carrying the uracil-forming reaction using a "methyl" benzylcarbamate such as Ia as opposed to using an "ethyl" benzylcarbamate such as Ib. The yields of these reactions were reproducible within about five to six percent. Surprisingly, the inventors found that formation of the benzyluracil starting with a methyl benzylcarbamate proceeds in much higher yield than the same reaction starting with the corresponding ethyl carbamate.

What is claimed:

1. A method for preparing a benzyluracil comprising the steps of taking an ester of 3-amino-4,4,4-trifluoro-2-butenoic acid, forming an alkali metal salt of the ester, contacting the salt in the presence of a suitable solvent with a methyl (optionally substituted-benzyl)carbamate of formula I to provide a benzyluracil of formula II:

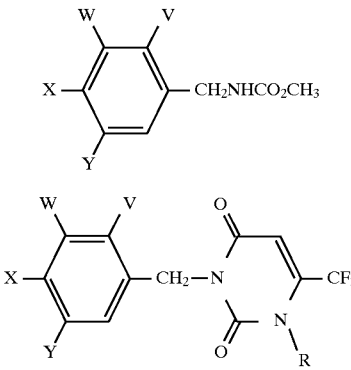

in which V is hydrogen, halogen, nitro, amino, alkoxy, alkyl, cyano, phenyl, alkylcarbonylamino, alkylsulfinyl, or haloalkyl;

W is hydrogen, halogen, alkyl, alkoxy, alkylaminocarbonyl, propargyloxy, cyano, nitro, benzoyl, aminooxycarbonyl, alkylsulfonyl, alkoxyiminoalkyl, alkylthio, or alkylsulfinyl;

X is hydrogen, chlorine, alkoxy, nitro, or amino;

Y is hydrogen, halogen, alkyl, haloalkyl, alkoxy, haloalkoxy, alkoxyalkyl, alkylthio, alkylthioalkyl, alkenyl, acyl, epoxyalkyl, cyano, alkylaminocarbonyl, carboxy, formyl, hydroxy, hydroxyalkyl, haloalkylsulfonyloxy, benzoyl, aminooxycarbonyl, alkoxycarbonyl, propargyloxy, alkylsulfonyl, alkylsulfinyl, alkoxyiminoalkyl, dialkylaminocarbonylthio, or X and Y taken together are —OCH₂O— or —OC(CH₃)₂O—; and R is hydrogen, sodium, potassium, lithium, barium or calcium.

2. A method of claim 1 comprising the further step of contacting II with a methylating agent in the presence of a suitable solvent to provide II where R is methyl.

3. A method of claim 2 where V is chlorine, W is chlorine or methoxy, X is hydrogen, and Y is chlorine or methoxy.

4. A method of claim 3 where the alkali metal salt is the sodium or potassium salt.

5. A method of claim 4 where the ester of the butenoic acid is ethyl 3-amino-4,4,4-trifluoro-2-butenoate.

6. A method of claim 5 where V and Y are chlorine and W is methoxy.

* * * * *